United States Patent
Picollet-D'Hahan et al.

(10) Patent No.: US 7,521,255 B2
(45) Date of Patent: Apr. 21, 2009

(54) METHOD AND DEVICE FOR CONTROLLING THE POSITIONING OF A BIOLOGICAL ELEMENT ON A SUPPORT

(75) Inventors: Nathalie Picollet-D'Hahan, La Ferriere (FR); Patrick Chaton, Theys (FR); Stephane Getin, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/590,496

(22) PCT Filed: Feb. 23, 2005

(86) PCT No.: PCT/FR2005/050118

§ 371 (c)(1),
(2), (4) Date: Jan. 17, 2007

(87) PCT Pub. No.: WO2005/085841

PCT Pub. Date: Sep. 15, 2005

(65) Prior Publication Data

US 2007/0161049 A1      Jul. 12, 2007

(30) Foreign Application Priority Data

Feb. 26, 2004    (FR) .................................. 04 50356

(51) Int. Cl.
*G01N 21/76* (2006.01)
*C12M 1/34* (2006.01)

(52) U.S. Cl. ...................... 436/172; 435/288.7; 385/33; 385/37

(58) Field of Classification Search ................. 436/527, 436/805, 535; 422/56, 57, 58, 59; 435/288.7; 385/33, 37

See application file for complete search history.

(56) References Cited

U.S. PATENT DOCUMENTS 4,558,014 A * 12/1985 Hirschfeld et al. .......... 436/527

(Continued)

FOREIGN PATENT DOCUMENTS

EP          1 067 378          1/2001

(Continued)

OTHER PUBLICATIONS

Picollet-D'Hahan, Nathalie et al., "Multi-Patch: A chip-based ion-channel assay system for drug screening", Proceedings of the International Conference on MEMS, NANO and Smart Systems (ICMENS'03), pp. 251-254, 2003.

(Continued)

*Primary Examiner*—Nelson Yang
(74) *Attorney, Agent, or Firm*—Oblon, Spivak, McClelland, Maier & Neustadt, P.C.

(57) ABSTRACT

A method for controlling directly and in real time positioning of a biological element on a zone of a support, in which the biological element is labeled with a tracer that emits a light radiation and the zone of the support is located in a layer of a material capable of trapping the light radiation. The biological element is positioned on the zone of the support. The intensity of the light radiation trapped in the layer is measured. The positioning of the biological element is determined by comparing the intensity thus measured with at least one reference value. The above operations can be carried out successively or simultaneously. A device can apply the method to the positioning of one or more biological elements on one or more zones of a support.

9 Claims, 5 Drawing Sheets

U.S. PATENT DOCUMENTS

2003/0092075 A1* 5/2003 Pepper .................. 435/7.9

FOREIGN PATENT DOCUMENTS

| WO | 00/34776 | 6/2000 |
|---|---|---|
| WO | 01/25769 | 4/2001 |
| WO | 01/59447 | 8/2001 |
| WO | 02/10747 | 2/2002 |

OTHER PUBLICATIONS

Lieberherr, M. et al., "Optical-Environment-Dependent Effects on the Fluorescence of Submonomolecular Dye Layers on Interfaces", Surface Science, vol. 189/190, pp. 954-959, 1987.

Dubertret, Benoit, "quantum dot", vol. 19, No. 5, pp. 532-534, 2003.

* cited by examiner

METHOD AND DEVICE FOR CONTROLLING THE POSITIONING OF A BIOLOGICAL ELEMENT ON A SUPPORT

TECHNICAL FIELD

The invention relates to a method for controlling directly and in real time the positioning of a biological element on a zone of a support on which it is intended to be positioned.

It also relates to a device for applying this method to the positioning of one or more biological elements on one or more zones of a support.

In the above text and subsequent text, the term "biological element" is intended to mean any natural or artificial element, at least part of which consists of a biological membrane or reproduces the functional characteristics of a biological membrane.

Thus, it may be a cell or a cellular organelle of the type vacuole, golgi apparatus, mitochondrion, endoplasmic reticulum, lysosome, etc., a biological membrane fragment, possibly accompanied by cytosolic parts, an artificial lipid bilayer such as a phosphatidylcholine or phosphatidylglycerol film, having one or more protein pores, or else a biomimetic membrane.

The method and the device according to the invention make it possible, in particular, to verify the establishment of a high-resistance sealing between a biological element and a zone of a support by means of the patch-clamp technique.

They are therefore capable of constituting tools of choice in all fields where the patch-clamp technique is itself liable to be used.

By way of examples of applications of this technique, mention may be made of:
- pharmaceutical research, in particular for studying the mechanisms responsible at the cellular level for pathologies related to an ion channel dysfunction; the identification of the sites and the methods of action of medicaments known to be effective in the treatment of these pathologies; the medium- or high-throughput screening of molecules which have ion channels as their targets and which may, as a result, be of therapeutic interest, or of candidate medicaments for which it is desired to evaluate the effects and/or the toxicity; the development of antidotes against poisons or venoms;
- the medical field, in particular for the diagnosis of pathologies related to an ion channel dysfunction;
- industry, in particular the agrofoods industry, pharmaceutical industry and cosmetics industry, especially for hygiene control of production lines and of the products which are derived therefrom;
- the environmental field, in particular for the detection of pollutants;
- the fundamental research, for example for the study of mechanosensitive ion channels with a view to the development of "mechanical" sensors; the detection of live cells or cells which have conserved their membrane integrity, or, on the contrary, of dead cells or cells which have lost their membrane integrity; the measurement of a modification of membrane capacitance subsequent to the fusion of a cell with another cell or a vesicle; the stimulation of cells such as neurons with a view, for example, to studying, promoting, or even accelerating, neuronal regeneration, regrowth or plasticity; the study of the intracellular activity of a cell network, of a tissue or of a cell coculture, the study of the response of cells A to the application of an electrical stimulation to cells B or else the study of the function of an ion channel by blocking the expression of the gene encoding this protein, subsequent to the introduction into the cell of molecules such as an antisense DNA or an siRNA (small interfering RNA).

PRIOR ART

The patch-clamp technique, developed by NEHER and SAKMANN in 1981, remains, to date, the most effective technique for controlling the differences in transmembrane electric potential in a fragment of plasma membrane or a whole cell and, consequently, for gaining direct access to ion fluxes circulating in the ion channels of this membrane fragment or of this cell.

As initially designed, it consists in applying the lower end of a glass micropipette to the plasma membrane of a cell and in establishing, by applying an oral suction at the upper end of the micropipette, a high-resistance seal, of the order of 1 to 10 gigaohms (hence the fact that it is usually referred to as "gigaseal"), between the lower end of the micropipette and the membrane fragment with which it is in contact ("cell-attached" configuration).

The suction can be pursued until opening of this membrane fragment is obtained ("whole-cell" configuration). The latter can also be isolated from the rest of the cell by mechanical excision: in this case, reference is made to "excised patch".

It is then possible, by applying a constant electric voltage to the membrane fragment or to the cell and recording the variations in this voltage, to measure the electrical activity resulting from a change in state (opening or closing) of the ion channels located on the entire cell membrane (in the "whole-cell" configuration) or on the sole membrane fragment or even on a sole ion channel (in the "cell-attached" or "excised patch" configuration).

In order to facilitate the implementation of this technique and to make it more effective, a certain number of teams have focused, in recent years, on developing devices, and in particular biochip-type miniaturized devices, intended to measure the transmembrane ion exchanges of several cells in parallel according to the patch-clamp principle.

These devices generally comprise a flat substrate which is microstructured, i.e. equipped with micrometric wells, onto which the cells are deposited, and also one or more channels which make it possible, through the actuation of a pump, to create a suction at the base of these wells and to thus produce a gigaseal between the substrate and a fragment of the plasma membrane of these cells.

Such devices are, for example, described in WO 01/25769 [1] and in WO 01/59447 [2].

Irrespective of whether the patch-clamp technique is carried out conventionally, i.e. by means of a glass micropipette, or on a biochip, the reliability of the results obtained depends mainly on the success of the gigaseal, the latter in fact conditioning the stability of the attachment between the support and the cell membrane, the electrical insulation of the membrane fragment, the correct application of an electric potential to this fragment and the validity of the measurement of the resulting electric current. Now, the gigaseal is relatively difficult to obtain: thus, the success rate is approximately 40% to 50% in conventional patch-clamp, and approximately 20% for biochips.

At the current time, the establishment of a gigaseal is monitored and controlled by means of electrical resistance measurements since the invagination of a fragment of cell membrane in the end of a micropipette or at the base of a microwell, and then the sealing of this fragment on this end or this base have the effect of creating a resistance to the passage of an electric current.

These measurements have the major drawback of not allowing a direct control of the establishment of the gigaseal since they require the application of successive voltage pulses and calculation of the resistance variations, in the knowledge that the increase in resistance can be rapid or slow, according to the law of all-or-nothing, or can be very gradual. Furthermore, in the case of a biochip, they require the recording, in parallel, of the variations in resistance in all the wells, before identifying those in which a gigaseal has become established, and then returning to the "positive" wells so as to then apply the ion channel activation protocols.

The inventors therefore set themselves the aim of providing a method which makes it possible to control directly and in real time the positioning of a biological element on a zone of a support on which it is intended to be positioned, and, in particular, the sealing of this biological element on this zone, both when the support is cylindrical like the micropipettes used in the conventional patch-clamp technique and when it is flat, like the supports which go to make up biochips.

They also set themselves the aim of providing a device for applying this method to the positioning of one or more biological elements on one or more zones of a support.

DISCLOSURE OF THE INVENTION

This aim, and others also, are achieved by means of a method for controlling the positioning of a biological element on a zone of a support, in which, this biological element being labelled with a tracer which emits a light radiation and the zone of the support on which it must be positioned being located in a layer of a material capable of trapping this light radiation:

a) the biological element is allowed to become positioned on the zone of the support;

b) the intensity of the light radiation trapped in said layer is measured; and c) the positioning of the biological element is determined by comparing the intensity value thus measured with at least one reference value; it being possible for steps a), b) and c) to be carried out successively or simultaneously.

Thus, the method according to the invention consists of an optical control of the positioning of the biological element relative to the zone of the support on which it is intended to be positioned, and in particular of a monitoring of this positioning over time.

This optical control is based on the property, exhibited by a radiation emitted by a light source, of behaving differently in a layer of a material that is more refringent than the medium in which it is emitted, according to the distance which separates said light source from the surface of this layer.

Figure 1:
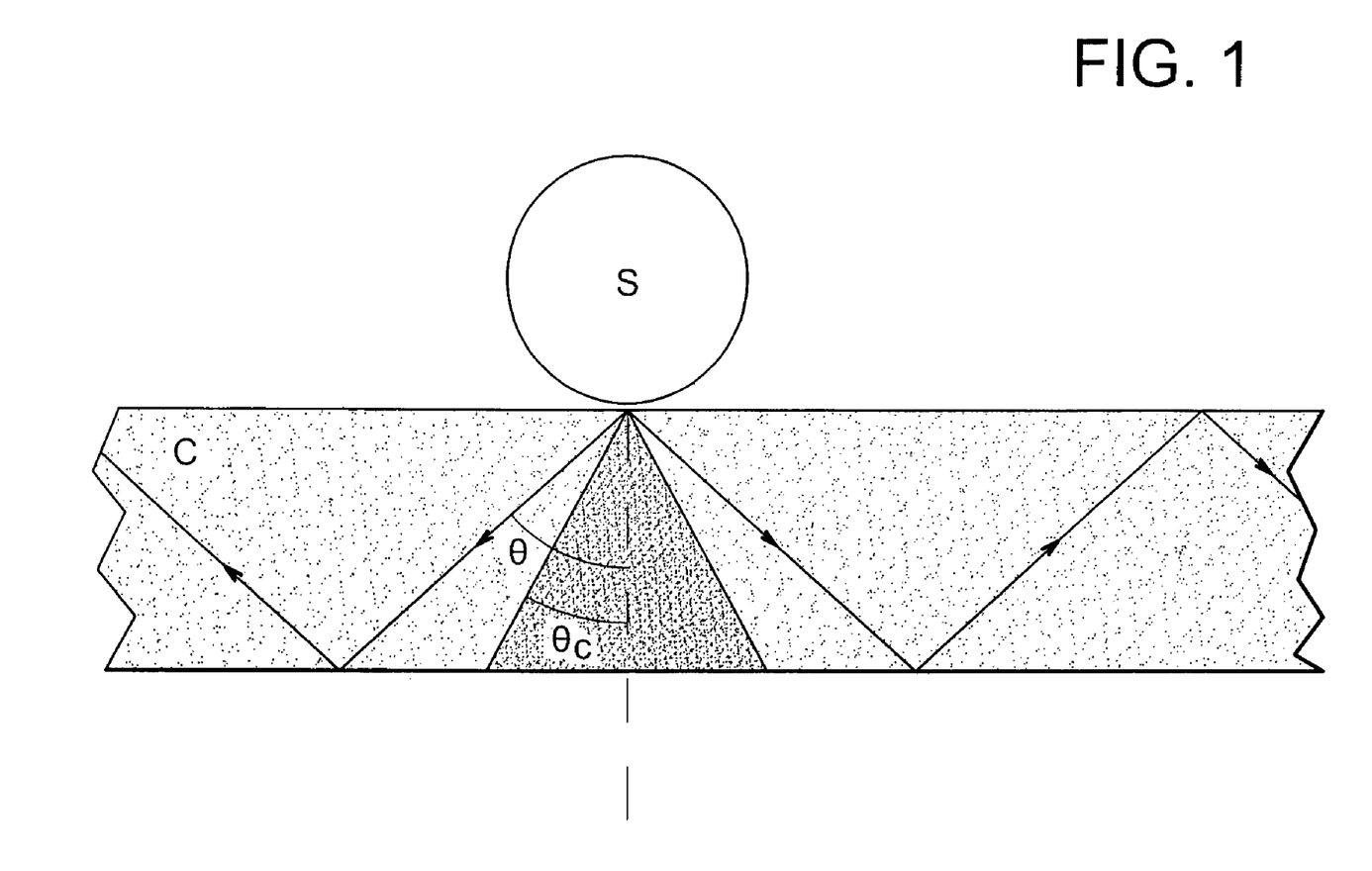
FIG. 1, already described, illustrates the behaviour of the rays emitted by a light source such as a fluorophore, when this source is sufficiently close to the surface of a layer of a material which is more refringent than the medium in which it is situated.

In fact, as shown experimentally by M. Lieberherr et al., in *Surface Science*, vol. 189/190, 954-959, 1987 [3], and illustrated in FIG. 1 attached in the annex, when a light source S such as a fluorophore is sufficiently close to the surface of a layer C of a material, for example a few nanometres from this surface, the angle of refraction $\theta$ of the rays from this source in the layer C is beyond the critical angle $\theta c$. It is, moreover, well known that light rays which have such an angle propagate in the layer C in total reflection.

Thus, the light intensity trapped in the material is a function of the distance which separates the light source from the surface of the layer and measurement thereof makes it possible to assess this distance.

In accordance with the invention, the biological element is preferably labelled with a fluorescent tracer, although other types of tracers can be used, such as bioluminescent or chemiluminescent tracers, provided that they can be attached to or expressed at the surface of a biological element.

This fluorescent tracer can be in very diverse forms.

Thus, for example, it can in particular be an organic fluorophore such as fluorescein and its derivatives (fluorescein isothiocyanate, for example), Oregon green, rhodamine and its derivatives (tetra-methylrhodamine isothiocyanate, for example), Texas red, Bodipy, cyanine and its derivatives (Cy 3.5, for example), which is chemically coupled to one or more membrane proteins of the biological element.

It may also be an antibody labelled with one of these fluorophores, which is directed against a membrane protein of the biological element and which is attached to this element by means of an antigen-antibody reaction, or a fluorescent membrane protein such as green fluorescent protein (GFP), extracted from the jellyfish *Aequorea victoria*, and its derivatives of various colours (cyan, yellow and blue), which is expressed by the biological element after transfection of the latter with the cDNA encoding this protein.

All these fluorescent tracers and the protocols for using them are well known to those skilled in the art and are referenced in commercial catalogues such as those of the companies Molecular Probes and Clontech.

The biological element can also be labelled with a mineral fluorescent tracer such as a "quantum dot", as described by B. Dubertret in *M/S* No. 5, vol. 19, 532-534, 2003 [4].

As indicated above, the zone of the support on which the biological element must be positioned is located in a layer of a material capable of trapping the light radiation emitted by the biological element, more simply referred to hereinafter as "the layer".

In the context of the present invention, the expression "material capable of trapping the light radiation emitted by the biological element" is intended to mean any material having the double property of being transparent to the type of light radiation emitted by the biological element so as to allow the propagation thereof, and of having a refractive index greater than the refractive index of the media located on either side of the propagation medium at the moment when the positioning of the biological element on the zone of the support is desired, and in particular of the medium in which the biological element is situated.

It is desirable for this material to also be biocompatible and for it not to emit, itself, a light radiation, in any event one of the same wavelength as the light radiation emitted by the biological element, so as not to interfere with the latter.

Thus, for example, if the biological element is labelled with a tracer which emits a visible light, such as a fluorescent tracer, and if the medium in which it is situated is a physiological medium (saline aqueous medium with a refractive index $\approx 1.33$ for visible light), the material forming the layer can be an organic or mineral glass, in particular glass, silica, silicon nitride ($Si_3N_4$), titanium dioxide ($TiO_2$), hafnium dioxide ($HfO_2$), alumina ($Al_2O_3$), silica loaded with potassium or silver ions, for example by ion exchange, or one of the very numerous synthetic polymers proposed on the market which exhibit high percentages of transmission of visible light (in practice, of the order of 90% or above), combined with refractive indices of 1.5 or more.

By way of examples of such polymers, mention may be made of polydimethylsiloxanes, poly(methyl methacrylates)s, more well known under the name plexiglas® and altuglas®, high-fluidity polycarbonates, such as those sold by the companies Bayer, Dow or GE Plastics, or else cyclic olefinbased copolymers such as those sold by the companies Ticona and Mitsui Chemical Industries.

In accordance with the invention, step a) of the method can consist in allowing this biological element to take its place on the zone of the support, for example by simple sedimentation, or, on the contrary, in acting on this element so as to facilitate, accelerate or optimize its positioning, for example by application of a pressure field, of an electric field, or the like.

In step b), the measurement of the intensity of the light radiation trapped in the layer involves this radiation being extracted from this layer beforehand, i.e. it being led to re-exit this layer after having propagated therein by internal reflection.

In accordance with the invention, this extraction can be carried out by means that the support permanently comprises, or with which the latter is temporarily provided before carrying out the measurement of the intensity of the trapped light radiation, or even before allowing the biological element to become positioned when steps a) and b) are not carried out simultaneously.

Thus, the method according to the invention can comprise, prior to step a) or between steps a) and b), a step consisting in providing the support with means for extracting the light radiation trapped in the layer. These extraction means are described later.

Moreover, in step b), the measurement of the light radiation trapped in the layer can be optimized by the presence of means suitable for collecting the light radiation extracted from this layer before its intensity is measured, such as convergent lens(es), mirror(s) optionally combined with one or more lenses, matrix of microlenses and/or of micromirrors, or the like.

Thus, the method according to the invention can also comprise, prior to step a) or between steps a) and b), a step consisting in placing, opposite the layer, means for collecting the light radiation extracted from this layer if such means are not initially present.

Step b) of the method can be carried out by any system for detecting and quantifying a light radiation, such as, for example, a point sensor of the photomultiplier tube or photodiode type, or an image sensor such as a video tube, a CCD camera, a CMOS camera or a photodiode camera.

As regards step c), it can in particular consist in comparing the intensity value measured with a standard curve expressing the variation in light intensity trapped in the layer as a function of the position of the biological element relative to the zone of the support on which it must be positioned, established beforehand under identical experimental conditions.

In accordance with the invention, the positioning of the biological element on the zone of the support preferably comprises the sealing of this element on said zone.

When the zone of the support on which the biological element must be sealed consists of the edges of a through-opening made in this support, then step a) of the method according to the invention preferably comprises the creation of a low pressure in this opening suitable for allowing the biological element to partially penetrate therein and to become sealed on its edges.

In such a case, steps a), b) and c) are preferably carried out simultaneously so as to control the quality of the sealing as the latter becomes established.

As indicated above, the biological element may be any natural or artificial element, at least part of which consists of a biological membrane or reproduces the functional characteristics of a biological membrane, for instance a cell or a cellular organelle such as vacuole, golgi apparatus, mitochondrion, endoplasmic reticulum, lysozyme, etc., a biological membrane fragment, possibly accompanied by cytosolic parts, an artificial lipid bilayer such as a phosphatidylcholine or phosphatidylglycerol film, having one or more protein pores, or else a biomimetic membrane.

The biological element is preferably a cell.

A subject of the invention is also a device for controlling the positioning of at least one biological element on at least one zone of a support, which comprises:

a support comprising a layer of a material capable of trapping a light radiation designed to be emitted by said biological element, and means for extracting the light radiation trapped in said layer, said zone of the support being located in said layer; and means for measuring the intensity of the light radiation extracted from said layer.

According to a first preferred embodiment of the device, the support is a tube open at both its ends and the zone on which the biological element must be positioned is one of the two openings of this tube.

In this case, the support is preferably a micropipette, and in particular a micropipette suitable for the implementation of the patch-clamp technique.

According to another preferred embodiment of the device, the support is a planar support, i.e. with a general shape which is planar, and the zone on which the biological element must be positioned is an opening that this support comprises, which opening can consist of a more or less pronounced depression, hollowed out in one of the faces of the support, or can be a through-opening, i.e. extending from one face to the other of the support.

In the latter case, the support is preferably a support suitable for the implementation of the patch-clamp technique.

As indicated above, the layer of material capable of trapping the light radiation, more simply referred to hereinafter as "the layer", can in particular be made of an organic or mineral glass, of silica, of silicon nitride, of titanium dioxide, of hafnium dioxide, of alumina, of silica loaded with potassium or silver ions, or of a synthetic polymer.

This layer can, moreover, extend over the entire thickness of the support or, on the contrary, constitute only a part thereof, provided that the other material(s) constituting the support which is (are) in contact therewith have a refractive index lower than that of the material of which it is made. In any event, it has a thickness of at least 200 nm.

In accordance with the invention, the means for extracting the light radiation trapped in the layer comprise any configuration of the support or any element associated with this support which makes it possible to interrupt the propagation of the light radiation in this layer and to cause it to re-exit therefrom.

Thus, these extraction means can in particular consist of a raised area or a hollow or a series of raised areas and of hollows made in one of the faces of the layer, or of a component which is placed on one of the faces of the layer and which forms, on this face, a raised area or a series of raised areas and of hollows, it being possible for this part to be detachable from or integral with said layer.

They may also consist of a material which is deposited onto one of the faces of the layer, at one or more points of this face, it being possible for this material to be in the form of a liquid, of a gel or of a solid.

They may also consist of an interruption of the layer by a material which is opaque with respect to the light radiation.

When the support is a planar support, the extraction means preferably extend all the way around this support on which the biological element must be positioned.

Preferably, the device according to the invention also comprises means for collecting the light radiation extracted from the layer, such as convergent lens(es), mirror(s), optionally associated with one or more lenses, matrix of microlenses and/or micromirrors, or the like.

As indicated above, the measuring means can comprise any system for detecting and quantifying a light radiation, such as, for example, a photomultiplier tube, a photodiode, a video tube, a CCD camera, a CMOS camera or a photodiode camera.

The device according to the invention can also comprise means for excitation of one or more fluorophores when the light radiation designed to be emitted by the biological element is a fluorescent radiation.

In a particularly preferred embodiment of the device according to the invention, the support is a planar support which comprises a plurality of zones for the positioning of a plurality of biological elements, in which case:

the layer of material capable of trapping the light radiation is divided up into as many parts as there are zones on the support;

each zone of the support is located in one of these parts;

these parts are separated from one another by means suitable for preventing the light radiation from propagating from one part to the other; and for each part of said layer, the support comprises means for extracting the light radiation trapped in this part, while the device comprises means for collecting the light radiation extracted from this part and means for measuring the intensity of the light radiation collected by said collecting means.

In this preferred embodiment, the layer capable of trapping the light radiation is preferably supported by a layer of a material which is opaque with respect to this light radiation, and the parts of the layer capable of trapping the light radiation are separated from one another by projections from the layer which is opaque with respect to the light radiation, which extend into the thickness of the layer capable of trapping the light radiation.

The device according to the invention can be integrated into a more complex system of analysis, in particular into a system for jointly measuring the electrical activity of one or more biological elements.

In particular, it can be associated with:

electrodes connected to a circuit for power supply and for measuring an electrical quantity, and suitable for allowing the application to the biological elements of an electric voltage and the recording of the variations in this voltage subsequent to a change in state (opening or closing) of the ion channels of these biological elements;

capillaries, optionally connected to a system for distributing liquids and/or to a system for suctioning liquids, and suitable for allowing the introduction of substances at the biological-element-positioning zones or, on the contrary, the removal of such substances, or else the changing of the composition of the study media (purge).

Another subject of the invention is the application of a method as defined above, or of a device as defined above, to the control of the establishment of a high-resistance seal between at least one biological element and at least one zone of a support by means of the patch-clamp technique.

The invention will be understood more clearly on reading the additional description which follows, which relates to various embodiments of a device in accordance with the invention and which refers to the attached drawings.

Of course, this additional description is given only by way of illustration of the invention.

BRIEF DESCRIPTION OF THE DRAWINGS

In FIGS. 2 to 8D, the identical elements were given the same references.

DETAILED DISCLOSURE OF SPECIFIC EMBODIMENTS

Figure 2:
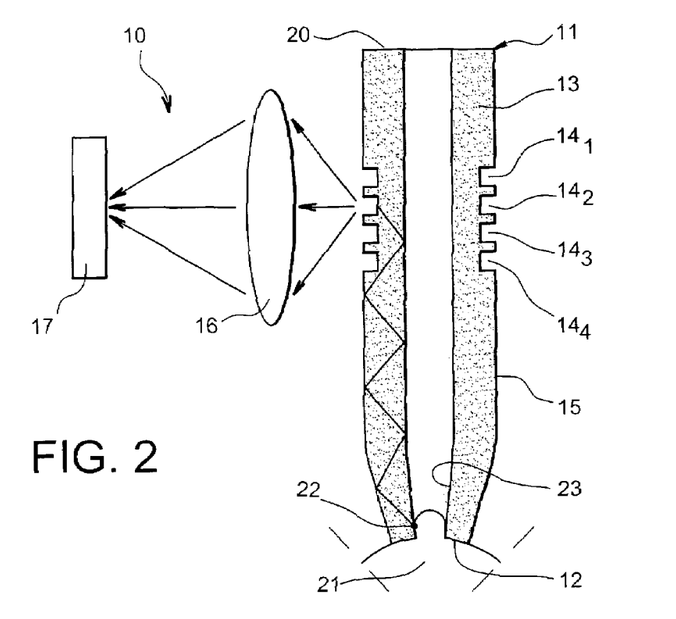
FIG. 2 is a schematic representation, in section, of a first embodiment of a device according to the invention designed to allow a control of the sealing of a biological element on the end of a micropipette by means of the conventional patch-clamp technique.

Reference is made first of all to FIG. 2, which schematically represents, in section, a first embodiment of a device 10 in accordance with the invention which is designed to allow the seal of a biological element by means of the conventional patch-clamp technique, i.e. by means of a micropipette, to be controlled.

Thus, in this embodiment, the support comprising a zone on which the biological element must be positioned is a micropipette, referenced 11 in FIG. 2.

Like conventional patch-clamp micropipettes, the micropipette 11 is in the form of a rigid tube, open at both its ends, which is limited by a wall 13 which has a substantially constant thickness, and one of the two end parts of which narrows.

The zone on which the biological element must be positioned consists of the end of the micropipette which has the smallest cross section, i.e. the end referenced 12 in FIG. 2. This end represents, under operating conditions, the lower end of the micropipette 11. It will therefore be referred to, in the subsequent text, as lower end, while the end 20, which is the end opposite, will be referred to as upper end.

Like conventional patch-clamp micropipettes, the wall 13 of the micropipette 11 can be made of glass, in which case this wall is capable of trapping any radiation, the wavelength of which is within the visible light spectrum, and in particular fluorescent radiation. It can also be made of any material exhibiting, like glass, rigidity, transparency to visible light and a higher refringence than the two types of media with which this wall is intended to be in contact under operating conditions, i.e. air and physiological solutions. Thus, it can in particular be made of a transparent polymer of the poly(methyl methacrylate) or polycarbonate type.

The micropipette 11 comprises, in its median part, means for extracting a light radiation trapped in the wall 13 under operating conditions.

In the embodiment illustrated in FIG. 2, these extraction means consist of a series of four annular grooves, respectively $14_1$, $14_2$, $14_3$ and $14_4$, separated by three ribs, which are identical to one another in shape and size, and which are made in the outer face 15 of the wall 13. By way of example, these grooves can be from a few angstroms to a few microns in depth and can extend over the wall 13 to a total height of a few microns to a few millimeters.

The device 10 also comprises means 16 for collecting the light radiation extracted from the wall 13 of the micropipette 11 under operating conditions. In the embodiment illustrated in FIG. 2, these collecting means consist of a convergent lens which is placed opposite a portion of the outer face 15 of the wall 13 of the micropipette 11 in which the grooves $14_1$ to $14_4$ are situated, but it could just as equally be a mirror, or a set of lenses and/or of mirrors, such as a matrix of microlenses and/or of micromirrors.

The device 10 also comprises means 17 for measuring the intensity of a light radiation collected by the collecting means 16 under operating conditions, which are placed opposite the collecting means. These measuring means can in particular comprise a point sensor such as a photomultiplier tube or photodiode, or an image sensor such as a video tube, a CCD camera, a CMOS camera or a photodiode camera.

The use of the device 10 for controlling the sealing of a biological element on the end 12 of the micropipette 11 is extremely simple.

As with a conventional micropipette, the lower end 12 of the micropipette 11 is first applied to a fragment of a biological element, for example a cell which will have been prelabelled with a tracer which emits a light radiation.

Then, by oral suction at the upper end 20 of the micropipette 11, a low pressure is created in the micropipette so as to cause this fragment to penetrate the opening that the lower end 12 of the micropipette 11 comprises, and to obtain sealing thereof on the wall 13, as illustrated in FIG. 2, which partially shows a fragment of a cell 21 thus sealed.

If these invagination and sealing processes take place correctly, they have the effect of bringing molecules of the tracer labelling the biological element to come first of all right up close, and then in contact, with the wall 13 of the micropipette 11, this contact being increasingly tight as the seal becomes established. This is reflected by an increase in the proportion of the rays which penetrate into the wall 13 of the micropipette 11 and which propagate therein, by internal reflection, to the extraction means $14_1$ to $14_4$, at which they are extracted from this wall, as illustrated in FIG. 2, which shows the course taken by a ray emitted by a molecule 22 of tracer which is in contact with the inner face 23 of the wall 13.

The rays extracted from the wall 13 of the micropipette 11 are then collected by the collecting means 16 and transmitted by the latter to the measuring means 17, which measure the intensity thereof.

Thus, if the invagination and sealing processes take place correctly, the light intensity measured by the measuring means 17 increases in the course of the suction so as to become optimal when the gigaseal is obtained.

Conversely, an inability to obtain a sustained increase in the light intensity measured by the measuring means 17 in the course of the suction or an abrupt break in this increase will signal poor mechanical holding of the seal or a loss of the integrity of the biological element or of the viability thereof if it is a living element (breaking up of the biological element, for example).

The micropipette 11 can have means for extracting the light radiation other than those shown in FIG. 2. By way of examples, FIGS. 3 to 6 illustrate five variants of realization of these extraction means.

Figure 3:
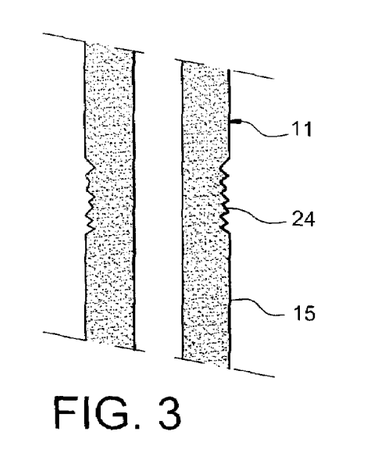
FIGS. 3 to 6 are partial schematic representations, in section, of the micropipette shown in FIG. 2, which illustrate five variants of realization of the means of extracting a light radiation that this micropipette comprises.

In the realization variant illustrated in FIG. 3, these extraction means consist of a rough annular zone 24 located in the outer face 15 of the wall 13 of the micropipette 11. By way of example, the bumps forming this zone, which can be made by a chemical or mechanical treatment, have a depth and a periodicity (distance between two peaks or between two hollows) of a few angstroms to a few tens of microns.

Figure 4:
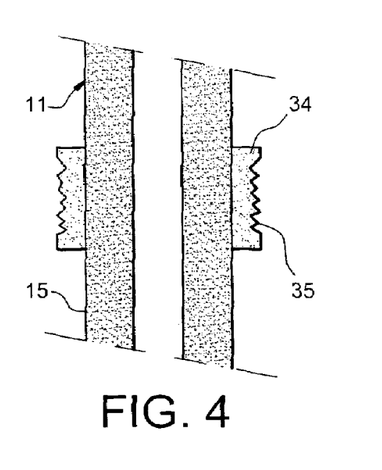

In the realization variant illustrated in FIG. 4, the extraction means consist of a ring 34 which surrounds the outer face 15 of the wall 13 of the micropipette 11 and which comprises, on its own outer face, a rough annular zone 35 of the same type as that previously described for FIG. 3.

Figure 5:
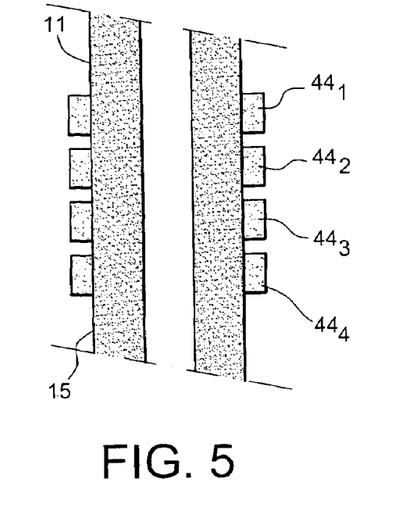
Figure 6:
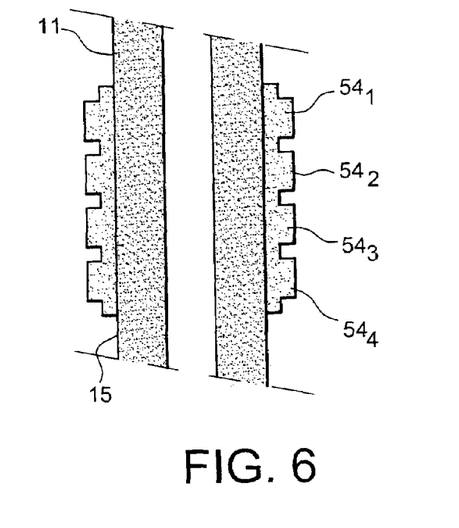

In the realization variant illustrated in FIG. 5, the extraction means consist of 4 rings, respectively $44_1$, $44_2$, $44_3$ and $44_4$, identical to one another in shape and size, and which are evenly distributed on the outer face 15 of the wall 13 of the micropipette 11, whereas, in the realization variant illustrated in FIG. 6, the extraction means consist of a single ring 54 which surrounds the outer face 15 of the wall 13 of the micropipette 11 and which comprises a series of three annular grooves $54_1$, $54_2$ and $54_3$ separated by ribs.

The rings 34, $44_1$ to $44_4$ and 54 shown in FIGS. 4 to 6 can be integral with the wall 13 of the micropipette 11, in which case they can either be all in one piece with this wall, or can be added on and attached to the latter. They can also be detachable, which can have a certain number of advantages such as that, for example, of being able to have a set of rings of different configurations and being able to choose the ring(s) most suitable for the operating conditions selected.

Moreover, the rings 34, $44_1$ to $44_4$ and 54 can be made of the same material as that which constitutes the wall 13 of the micropipette 11 or can be made of a different material.

Figure 7:
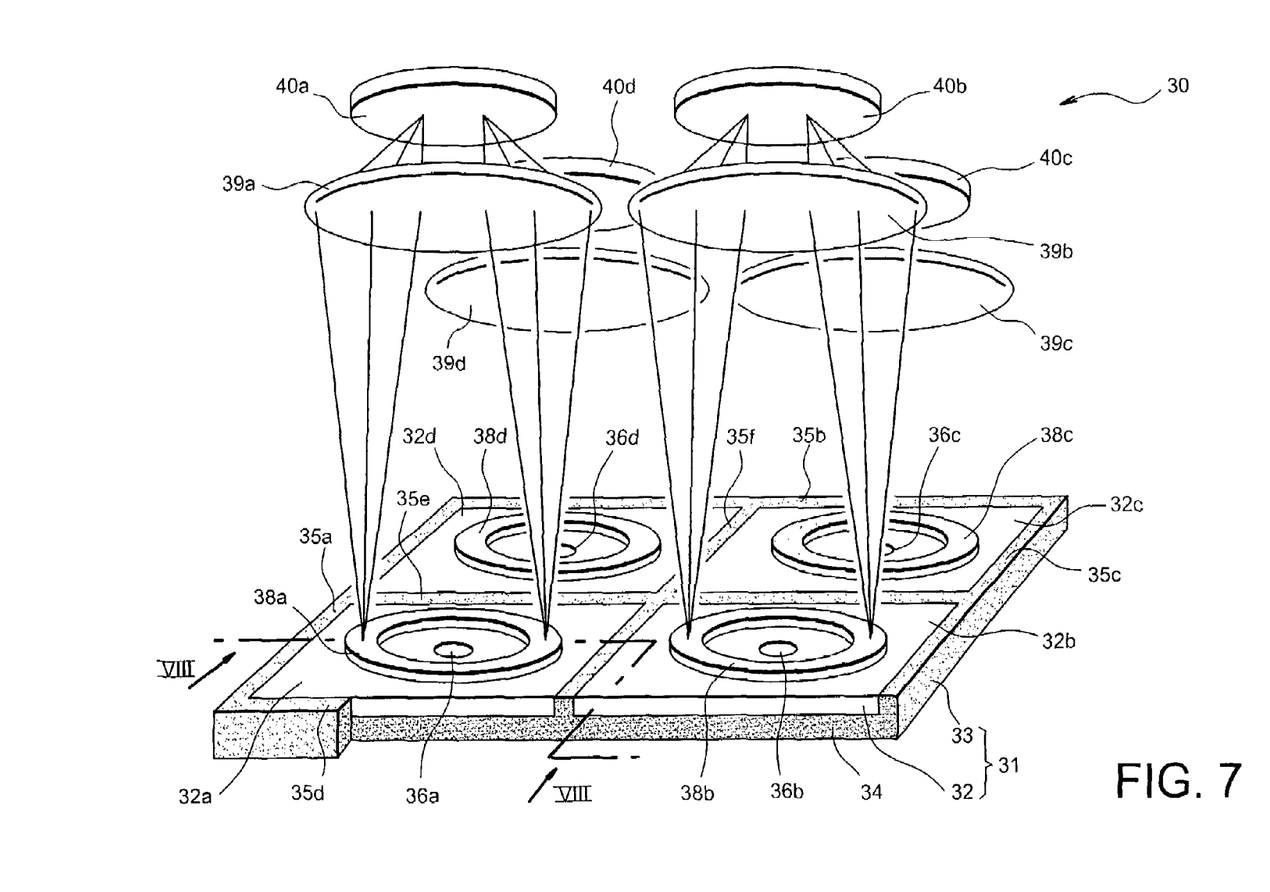
FIG. 7 is a schematic perspective representation of a second embodiment of a device according to the invention designed to allow a simultaneous control of the sealing of several biological elements on openings of a planar support by means of the patch-clamp technique.
Figure 8A:
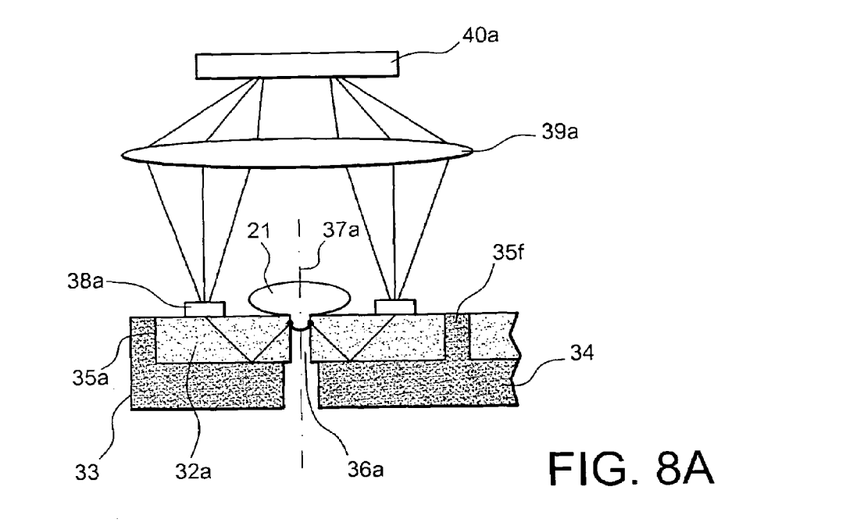
FIG. 8A is a partial schematic representation of the device shown in FIG. 7, seen in section along the line VIII-VIII.

Reference is now made to FIG. 7, which is a schematic perspective representation of a second embodiment of a device 30 according to the invention, which is designed to allow simultaneous control of the sealing of several biological elements on openings of a planar support by means of the patch-clamp technique, and also to FIG. 8A, which is a schematic and partial representation of this device, seen as a section along the line VIII-VIII.

As is visible in FIG. 7, the device 30 comprises a support 31 generally quadrangular in shape.

This support comprises a layer 32 which here is divided into four parts, respectively 32a, 32b, 32c and 32d, identical to one another in shape and size, but which could just as easily be divided up into a number of parts other than 4, the device 30 merely representing a nonlimiting example of a device according to the invention.

These four parts are recessed into a substrate 33 which comprises a base 34 and six walls erected vertically on this base, respectively 35a, 35b, 35c, 35d, 35e and 35f, together delimiting four cavities arranged like a grid and each housing one of the parts 32a to 32d of the layer 32.

Each part 32a to 32d of the layer 32 is equipped, at its centre, with a through-opening, respectively 36a, 36b, 36c or 36d, which communicates with an opening which is coaxial therewith and which crosses the base 34 of the substrate 33. The substrate 33 therefore also comprises four through-openings—one of these openings being visible in FIG. 8, in which it is referenced 37a—which can be connected to capillaries (not represented in FIGS. 7 and 8A) which can themselves be connected to a system for suctioning liquids such as a micropump.

Since the through-openings 36a to 36d of the layer 32 represent the zones of the support 31 on which the biological elements must be positioned, the layer 32 consists of a material capable of trapping a light radiation designed to be emitted by these elements, while the substrate 33 consists, itself, of a material which is opaque with respect to this radiation. Thus, for example, if the biological elements are designed to be labelled with a fluorescent tracer, the layer 32 may be a layer of glass, of silica, of $Si_3N_4$, of $TiO_2$, of $Al_2O_3$, or of a transparent polymer, while the substrate 33 can be made of a metal (Al, Au, Cu, Ag, etc.), of a semi-conductor (Si, Ge, etc.) or of an opaque polymer.

Each part 32a to 32d of the layer 32 is, in addition, equipped with means for extracting the light radiation trapped in this part under operating conditions.

In the embodiment of the device 30 shown in FIGS. 7 and 8A, these extraction means consist of rings, respectively 38a, 38b, 38c and 38d, which are placed on the upper face of the parts 32a to 32d and which surround the openings 36a to 36d. These rings, which may be present temporarily, i.e. for the period of time required to carry out the experiment, or permanently, can consist of a material in the form of a liquid, of a gel or of a solid and which is deposited onto the upper face of the parts 32a to 32d before the experiment or during it, or of a component which is integral with said parts 32a to 32d, it being possible for this component to be either all in one with these parts, or to be added on and attached to them.

As is visible in FIG. 7, the device 30 also comprises means for collecting the light radiation extracted by each of the rings 38a to 38d under operating conditions, respectively 39a, 39b, 39c and 39d, and also means for measuring the light radiation thus collected, respectively 40a, 40b, 40c and 40d. These collecting and measuring means can be of the same type as those mentioned above in relation to FIG. 2.

The use of the device 30 for simultaneously controlling the positioning and/or the sealing of biological elements on the openings 36a to 36d is also extremely simple.

After having deposited a biological element, for example a cell which will have been prelabelled with a tracer which emits a light radiation, onto or in proximity to each of the openings 36a to 36d, a low pressure is created in each opening of the substrate 33, for example by suction by means of the capillaries mentioned above, so as to cause a fragment of the biological elements to penetrate the openings 36a to 36d and to obtain sealing thereof on these openings, as illustrated in FIG. 8A, which shows a cell 21 thus sealed on the opening 36a of the layer 32.

Here also, if the invagination and sealing processes take place correctly, the light intensity measured by each of the measuring means 40a to 40d increases in the course of the suction so as to become optimal when the gigaseal is obtained.

The fact that the device 30 comprises, for each of the parts 32a to 32d of the layer 32 and, therefore, for each biological-element-positioning zone, means for extracting, collecting and measuring the light radiation trapped, which are independent of those provided for the other parts, makes it possible to rapidly and precisely identify the biological elements correctly sealed and those which are not, and, thus, to continue the experiment only on those for which the seal appears to be satisfactory, hence a considerable gain both in effectiveness and in time.

Figure 8B:
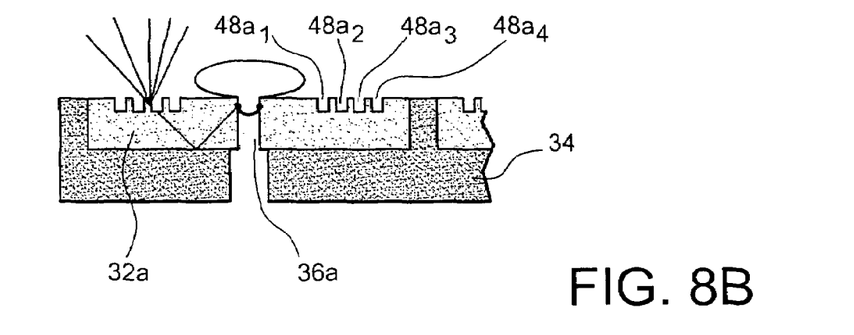
FIGS. 8B to 8D are partial schematic representations of the device shown in FIG. 7, seen in section along the line VIII-VIII, which illustrate three variants of realization of the means for extracting a light radiation that the support of this device comprises.
Figure 8C:
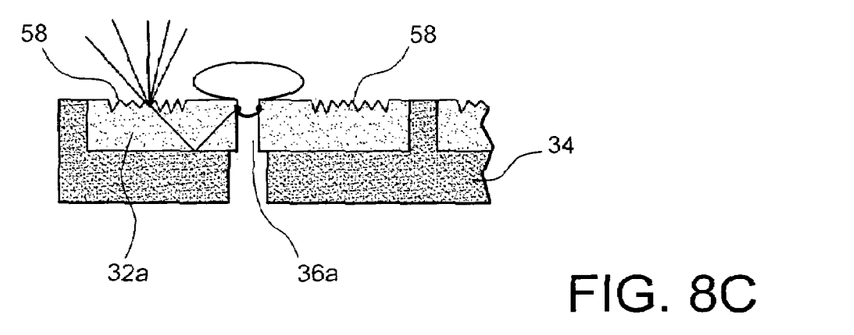
Figure 8D:
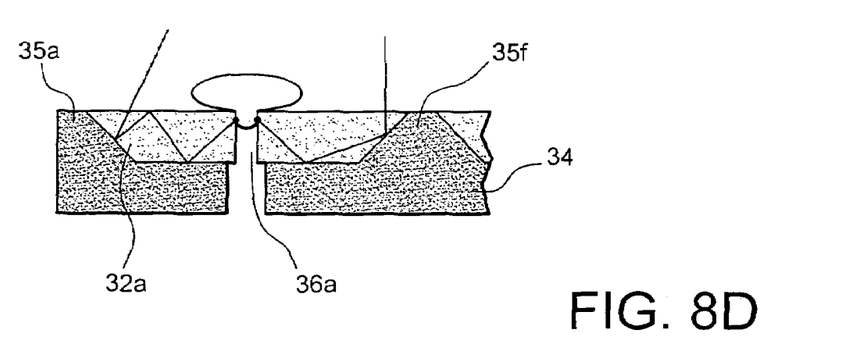

FIGS. 8B to 8D are partial schematic representations of the device shown in FIG. 7, seen in section along the line VIII-VIII, which illustrate three variants of realization of the means for extracting the light radiation.

In the variant illustrated in FIG. 8B, the extraction means consist of a series of four grooves, respectively $48a_1$, $48a_2$, $48a_3$ and $48a_4$, separated by three ribs, which are identical to one another in shape and size and which are made in the upper face of the part 32a of the layer 32, all around the opening 36a. By way of example, these grooves and ribs can have a periodicity of a few hundred nanometres to a few microns.

In the variant illustrated in FIG. 8C, the extraction means consist of a rough zone 58 made in the upper face of the part 32a of the layer 32, all around the opening 36a. By way of example, the bumps forming this zone, which can be made by chemical or mechanical treatment, can have a depth and a periodicity of a few angstroms to a few tens of microns.

Finally, in the variant illustrated in FIG. 8D, the extraction means consist of the side faces of the walls 35a and 35f of the substrate 33, the incline of which combined with the opacity of these walls are such that they direct the light radiation trapped in the part 32a of the layer 32 to the collecting means 39a (visible in FIG. 8A, but not represented in FIG. 8D).

REFERENCES CITED

[1] WO 01/25769
[2] WO 01/59447
[3] M. Lieberherr et al., *Surface Science*, vol. 189/190, 954-959, 1987
[4] B. Dubertret, *M/S* No. 5, vol. 19, 532-534, 2003.

The invention claimed is:

1. A method for controlling the formation of a seal between a biological element comprising a membrane and the edges of a through-opening in a support, wherein the biological element is labeled with a tracer that emits a light radiation, the support comprises a layer of a material configured to trap the light radiation by internal reflection, and the through-opening is located in the layer, the method comprising:
   a) forming the seal between the biological element and the edges of the through-opening by creating a low pressure in the through-opening to cause the biological element to partially penetrate the opening;
   b) measuring intensity of light radiation internally reflected in the layer at predetermined distances from the through-hole; and
   c) comparing the intensity thus measured with at least one reference value to determine when the seal is obtained;
wherein a) and b) can be carried out successively or simultaneously.

2. A method according to claim 1, in which the biological element is labeled with a fluorescent tracer.

3. A method according to claim 2, in which the fluorescent tracer is one of:
   a) an organic fluorophore chemically coupled to one or more membrane proteins of the biological element,
   b) an antibody labeled with an organic fluorophore, which is directed against a membrane protein of the biological element and which is attached to the biological element by an antigen-antibody reaction, and
   c) a fluorescent membrane protein which is expressed by the biological element.

4. A method according to claim 1, in which the layer of material capable of trapping the light radiation is made of one of the following:
   a) organic or mineral glass,
   b) silica,
   c) silicon nitride,
   d) titanium dioxide, e) hafnium dioxide,
f) alumina,
g) silica loaded with potassium or silver ions, and
h) a synthetic polymer.

5. A method according to claim 1, further comprising, prior to a) or between a) and b), providing the support with a means for extracting light radiation trapped in the layer of material capable of trapping the light radiation.

6. A method according to claim 5, further comprising, prior to a) or between a) and b), placing a means for collecting the light radiation extracted from the layer over the layer of material capable of trapping the light radiation.

7. A method according to claim 1, in which a) and b) are carried out simultaneously.

8. A method according to claim 1, in which the biological element is a cell.

9. A method for of establishing a high-resistance seal between a biological element comprising a membrane and the edges of a through-opening in a support by a patch-clamp technique, in which the biological element is labeled with a tracer that emits a light radiation, wherein the support comprises a layer of material configured to trap the light radiation by internal reflection, and the through-opening is located in the layer, the method comprising:
   a) forming the seal between the biological element and the edges of the through-opening by creating a low pressure in the through-opening to cause the biological element to partially penetrate the opening;
   b) measuring intensity of light radiation trapped in the layer; and
   c) comparing the intensity measured with at least one reference value to determine when the high-resistance seal is established;
wherein a) and b) can be carried out successively or simultaneously.

* * * * *